United States Patent [19]

Cousse et al.

[11] 4,246,271
[45] Jan. 20, 1981

[54] 4-PHENYL-2-THIAZOLYL-OXAMATES USEFUL IN THE TREATMENT OF ASTHMA

[76] Inventors: Henri Cousse, Foun de los Nobios Chemin de Lastinos; Gilbert Mouzin, 21, rue Sainte-Foy; Jean-Pierre Tarayre, Rue des Sports, Valdurenque, all of Castres, Tarn, France; Silvano Casadio, Via Tantardini 15, Milan, Italy, 20136

[21] Appl. No.: 48,371

[22] Filed: Jun. 14, 1979

[30] Foreign Application Priority Data

Jun. 19, 1978 [FR] France .................. 78 18500

[51] Int. Cl.³ .................................. C07D 277/38
[52] U.S. Cl. .................. 424/270; 548/195
[58] Field of Search ............... 424/270; 548/195, 196

[56] References Cited

U.S. PATENT DOCUMENTS

| 3,966,965 | 6/1966 | Sellstedt et al. | 424/309 |
| 4,054,666 | 10/1977 | Sellstedt et al. | 424/270 |

*Primary Examiner*—Nicholas S. Rizzo

*Attorney, Agent, or Firm*—Gordon W. Hueschen

[57] ABSTRACT

The present invention relates to new derivatives of 4-phenyl-2-thiazolyl oxamates having the formula:

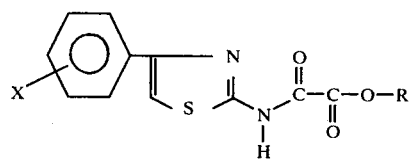

in which:
  X represents hydrogen, halogen, lower-alkyl, or lower-alkoxy.
  R is lower-alkyl or phenyllower-alkyl, e.g., benzyl.

These compounds, which have inhibiting properties on the passive cutaneous anaphylactic reaction, are useful in the treatment of asthma. Pharmaceutical compositions thereof and method of treating therewith.

11 Claims, No Drawings

4-PHENYL-2-THIAZOLYL-OXAMATES USEFUL IN THE TREATMENT OF ASTHMA

This invention, developed at the Pierre Fabre Research Center, concerns new derivatives of 4-phenyl-2-thiazolyl-oxamate, their preparation, and their application in therapy, particularly for the treatment of allergic asthma and of asthmatic bronchitis with allergic component.

The new chemical compounds have the general formula

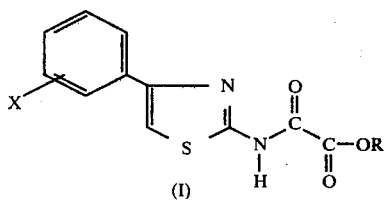

in which:

X, which is in 2, 3, or 4 position, represents hydrogen, lower-alkyl, lower-alkoxy, or halogen.

R represents lower-alkyl or phenyllower-alkyl, e.g., benzyl.

The compounds of general formula (I) can be prepared in two steps: by cyclization of a derivative of acetophenone by thiourea there are obtained the 2-amino-4-phenyl-thiazoles which, treated by an ester of oxalyl chloride, produce derivatives (I) in accordance with the reaction mechanism:

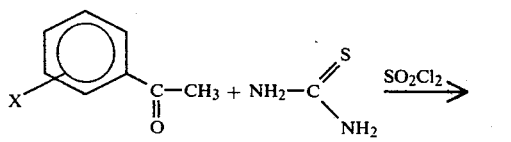

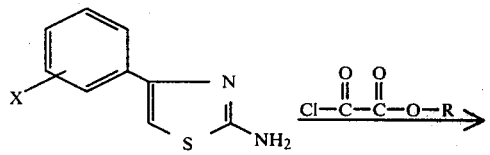

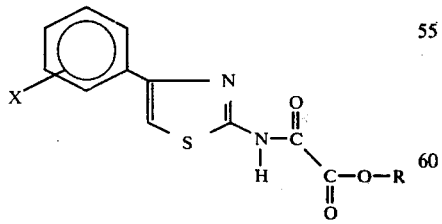

X and R having the meanings given above.

The following new chemical compounds and their method of preparation are cited by way of illustration and not of limitation.

EXAMPLE 1

Ethyl-(4-phenyl-2-thiazolyl)-oxamate (F 1863)

(a) 4-phenyl-2-amino-thiazole

Carefully mix 360 g (3 mols) of acetophenone and 455 g (6 mols) of thiourea and then add, in small portions, 264 ml (3.3 mols) of sulfuryl chloride.

The reaction is exothermic and the addition of the sulfuryl chloride takes two hours.

The reaction medium liquifies and then sets: bring it then to 105° C. for 3 hours.

Allow it to return to room temperature, wash with acetone and then filter.

Recrystallize the resultant crystals from 3 liters of boiling water. Recover the amine hydrochloride and treat it with a solution of ammonia of a pH of 12.

After filtration and drying, there are obtained 412 g of product (yield: 78%).

(b) Ethyl-(4-phenyl-2-thiazolyl)-oxamate (F 1863)

A suspension of 168 g (2 mols) of sodium bicarbonate in a solution of 352 g (2 mols) of 4-phenyl-2-amino-thiazole and 3.5 liters of acetone is agitated at room temperature. Add 272 g (2 mols) of ethyl chloroglyoxylate drop by drop and continue the agitation overnight.

After filtration, evaporate the ketone phase to dryness and recrystallize the yellow residue in a mixture of dioxane and alcohol. There are obtained 450 g of product (yield: 75%) of the formula

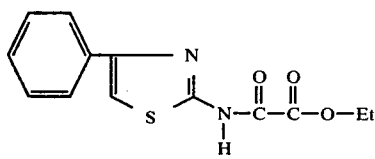

Empirical formula: $C_{13}H_{12}N_2O_3S$
Molecular weight: 276.31
Yellow crystals
Melting point: 158° C.
Thin-layer chromatography:
  support: silica gel 60 F 254 Merck
  solvent: acetic acid, dioxane, toluene 2/8/90
  development: UV and iodine
  Rf: 0.60
Solubilities: insoluble in water and in ethanol. 20% soluble in dimethyl acetamid and 25% soluble in methyl pyrrolidone.

EXAMPLE 2

Ethyl-(4-p-chlorophenyl-2-thiazolyl)-oxamate (F 1864)

(a) 4-parachlorophenyl-2-amino-thiazole

In a manner similar to that described in Example 1 but using parachloroacetophenone, there is obtained the product of the formula:

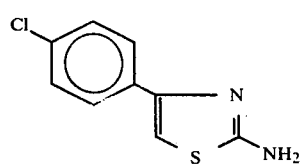

Empirical formula: $C_9H_7ClN_2S$

Molecular weight: 210.67
Crystals: yellow
Melting point: 167° C.
Thin-layer chromatography:
 support: silica gel 60 F 254 Merck
 solvent: acetic acid, dioxane, toluene 2/8/90
 development: UV and iodine
 Rf: 0.3
Solubilities: insoluble in water, 15% soluble in ethanol.

(b) Ethyl-(4-p-chlorophenyl-2-thiazolyl)-oxamate (F 1864)

To an iced solution containing 109.5 g of 2-amino-4-parachlorophenyl-thiazole in 2750 cc of anhydrous tetrahydrofuran and 157 cc of triethylamine, add 73 cc of ethyl chloroglyoxylate in solution in 50 cc of THF drop by drop with strong agitation and keep for 5 hours at room temperature. Evaporate the organic phase to dryness and wash with water. There is recovered, in a yield of 95%, 153.5 g of product of the formula:

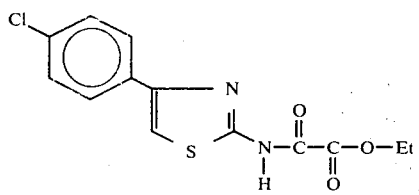

Empirical formula: $C_{13}H_{11}ClN_2O_3S$
Molecular weight: 310.76
Yellow crystals
Melting point: 252° C.
Thin-layer chromatography:
 support: silica gel 60 F 254 Merck
 solvent: chloroform-methanol 95/5
 development: UV and iodine
 Rf: 0.85
Solubilities: insoluble in water and in ethanol. 1% soluble in DMSO and 4% soluble in methyl pyrrolidone.

EXAMPLE 3

Ethyl-(4-paramethoxyphenyl-2-thiazolyl)-oxamate (F 1865)

(a) 4-Paramethoxyphenyl-2-amino thiazole

In a manner similar to that described in Example 1, but using paramethoxy acetophenone, there is obtained the product of the formula:

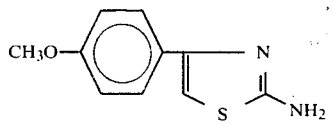

Empirical formula: $C_{10}H_{10}N_2OS$
Molecular weight: 206.27
Yellow crystals
Melting point: 209° C.

(b) Ethyl-(4-paramethoxyphenyl-2-thiazolyl)-oxamate (F 1865)

In a manner similar to that described in Example 2 but using 4-paramethoxyphenyl-2-amino-thiazole, there is obtained in a yield of 85% the product of the formula:

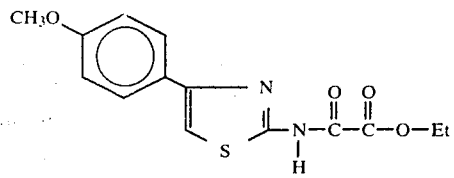

Empirical formula: $C_{14}H_{14}N_2O_4S$
Molecular weight: 306.34
Beige crystals
Melting point: 168° C.
Thin-layer chromatography:
 support: silica gel 60 F 254 Merck
 solvent: toluene, dioxane, acetic acid
 development: UV and iodine
 Rf: 0.67
Solubilities: insoluble in water and in ethanol. 50% soluble in dimethyl sulfoxide and 50% soluble in methyl pyrrolidone.

EXAMPLE 4

Benzyl-(4-metamethylphenyl-2-thiazolyl)-oxamate

In a manner similar to that described previously, but using metamethyl acetophenone and benzyl chloroglyoxylate, there is obtained the product of the formula:

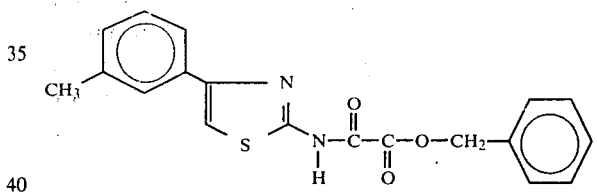

EXAMPLE 5

Benzyl-(4-orthobromophenyl-2-thiazolyl)-oxamate

In a manner similar to that described in the preceding examples but using orthobromo acetophenone and benzyl chloroglyoxylate there is obtained the product of the formula:

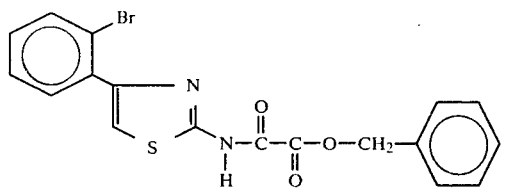

Where the foregoing examples produce a compound having a methyl or other lower-alkyl group, it is to be understood that compounds containing other lower-alkyl groups of straight or branched nature and preferably containing up to five carbon atoms, inclusive, such as methyl, ethyl, propyl, isopropyl, butyl, sec.-butyl, t.-butyl, amyl and isoamyl, are prepared in the same manner by substitution in the process of the appropriate different lower-alkyl starting material. Likewise, where chloro or other halogen atom is present, although chlorine is preferred, further halogen compounds including iodo, bromo, chloro, and fluoro compounds are prepared starting only from the appropriate halogenated starting material. Similarly, where methoxy or other lower-alkoxy group is present, compounds having other lower-alkoxy groups containing various lower-alkyl groups preferably having up to five carbon atoms inclusive, are prepared in the same manner from the appropriate different lower-alkoxy starting material. In the same manner, ortho and meta products are produced instead of the para by utilizing the selected ortho or meta substituted starting material and vice versa. Likewise, other R=phenyllower-alkyl compounds, wherein phenyllower-alkyl is representatively phenethyl, phenpropyl, phenbutyl, phenamyl, and the like, are readily prepared according to the identical reactions as given in the foregoing examples, starting only from the appropriately R-substituted starting material, e.g., phenethyl chloroglyoxylate. Similarly, other molecular changes within the scope of the invention are readily made.

EXPERIMENTS

The chemical compounds described above were subjected to toxicological, pharmacological and clinical experimentation in order to determine the possibilities of use in therapy.

(1) Toxicology (acute toxicity after a single oral administration in mice by the method of Miller & Tainter (Proc. Soc. Exper. Biol. Med., 1944, 57, 261)).

The products are administered in a suspension of Tween 80+distilled water. The mortality is noted at the end of 7 days. The following table summarizes the results obtained:

| Products | Doses in mg/kg | No. mice per lot | Mortality at end of 7th day | $LD_{50}$ approximate mg/L |
|---|---|---|---|---|
| F 1865 Example 1 | 1000 | 10 | 1 | >1000 |
| Example 2 F 1864 | 1000 | 10 | 0 | >1000 |
| Example 3 F 1865 | 1000 | 10 | 1 | >1000 |
| Example 4 | 1000 | 10 | 1 | >1000 |
| Example 5 | 1000 | 10 | 2 | >1000 |

(2) Pharmacodynamics

The results are obtained on the cutaneous passive anaphylaxis test in accordance with the method of Broeklehurst W. E. in Handbook of Experimental Immunology, Editor Weiz D. M., Blackwell Scientific Publications, Oxford and Edinborough, pages 754–751 (1967).

(a) Prepare the antiserum on rats sensitized by antigen; inject it intradermally.

(b) Leave a waiting time of 24 to 48 hours.

(c) Administration of the product to be tested per os 10 minutes before operation (d) (intravenous simultaneously with d).

(d) Intravenous injection of the antigen+stain.

(e) Sacrifice 30 minutes afterwards and visualize the antigen-antibody reaction by the leakage of the stain due to the increase of the capillary permeability under the combined influence of histamine and SRSA.

This action is expressed as $ED_{50}$, i.e., the dose which reduces by one-half the leakage of the stain as compared with the controls.

By way of illustration and not of limitation, we give below the results of two compounds designated by their code number:

| Product | $ED_{50}$ mg/kg per os |
|---|---|
| F 1863 | 1 |
| F 1865 | 2 |

The tests were carried out in succession with 30, 5, 1 and 0.2 mg/kg on homogeneous lots of 10 rats, with due consideration of their insolubility in water. These compounds are administered in suspension in Tween TM and water.

(3) Therapeutic Applications

With due consideration of the pharmacological properties, these compounds, and particularly compounds F 1863 and F 1865, can be used per os as a preventative for allergic attacks of asthma. These compounds may also be used in the treatment in urticaria, allergic rhinitis, and certain skin allergies, as well as other allergic manifestations, due to their allergic inhibitive characteristics.

For these various purposes, the compounds of the invention are, of course, administered in doses which vary with their nature, with the method of administration, and with the treatment desired.

Pharmaceutical preparations containing these active principles may be administered orally, parenterally, rectally, and locally, in each case for their intended purpose.

For oral administration tablets, capsules and elixirs may be used, the unit dose being 5 to 500 mg, in accordance with a usual maximum daily dose in man of 500 mg. For rectal administration these quantities are usually 100 to 500 mg respectively.

The pharmaceutical compositions may also contain other pharmaceutically and therapeutically compatible active principles.

A few examples of pharmaceutical preparations which contain a representative active principle forming an object of the invention are given below, by way of illustration only and not by way of limitation:

(a) tablets F 1863 or 1865 150 mg+excipient (b) suppository, adult, strong: F 1863 or 1865 200 mg+suppository excipient (c) capsules: F 1863 or 1865 75 mg plus excipient 100 mg; or F 1863 or 1865 alone.

For oral use, the compounds are usually administered as tablets, solutions, suspensions, or the like, in which they are present together with usual pharmaceutical carriers, excipients, binders, and the like. For example, tablets may be prepared conventionally by compounding one of the new compounds with customary carriers and adjuvants, e.g., talc, magnesium stearate, starch, lactose, gelatin, gums, and the like. In their most advantageous form, then, the compositions f the present invention will contain a non-toxic pharmaceutical carrier in addition to the active ingredient. Exemplary carriers are: Solids: lactose, magnesium stearate, calcium stearate, starch, terra alba, dicalcium phosphate, sucrose, talc, stearic acid, gelatin, agar, pectin, acacia, or other usual excipient; Liquids: peanut oil, sesame oil, olive oil, water, elixir, or other usual excipient. The active agents of the invention can usually be most conveniently administered in such compositions containing about 0.01 to 67 percent, preferably 0.04 to 12.15 percent, by weight of the active ingredient. Such formulations are representatively illustrated in U.S. Pat. No. 3,402,244.

A wide variety of pharmaceutical forms suitable for many modes of administration and dosages may be employed. For oral administration, the active ingredient and pharmaceutical carrier may, for example, take the form of a granule, pill, tablet, lozenge, elixir, syrup, or other liquid suspension or emulsion; and for rectal administration, a suppository. For topical or dermatological use and administration, an ointment, salve, solution, or suspension of usual type may be employed.

The method of using the compounds of the present invention comprises administering a compound of the invention, preferably admixed with a pharmaceutical carrier, for example, in the form of any of the above-mentioned compositions, or filled into a capsule, to alleviate one or more of the foregoing enumerated allergic conditions and symptoms, especially asthma, in a living animal body, whether human or domestic animal, for example, the aforementioned allergic asthma. The compounds are subject to usual variations in optimum daily and unit dosages, due to patient body weight, condition, and ancillary factors, and the invention therefore should not be limited by the exact ranges stated. The exact dosage, both unit and daily, will of course as usual have to be determined according to established veterinary and medical principles.

It is to be understood that the invention is not to be limited to the exact details of operation or exact compounds, compositions, or procedures shown and described, as obvious modifications and equivalents will be apparent to one skilled in the art, and the invention is therefore to be limited only by the scope of the appended claims.

We claim:

1. 4-phenyl-2-thiazolyl-oxamate derivatives having formula I

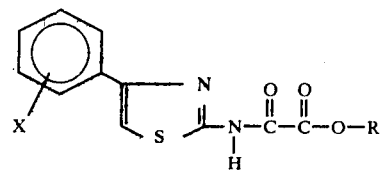

in which:
X which is in 2, 3, or 4 position represents hydrogen, halogen, lower-alkyl, or lower-alkoxy.
R represents lower-alkyl or phenyllower-alkyl.

2. A compound of formula I according to claim 1, characterized by the fact that it is selected from among:
ethyl-(4phenyl-2-thiazolyl)-oxamate
ethyl-(4-p-chlorophenyl-2-thiazolyl)-oxamate
ethyl-(4-p-methoxyphenyl-2-thiazolyl)-oxamate
benzyl-(4-m-methylphenyl-2-thiazolyl)-oxamate
benzyl-(4-o-bromophenyl-2-thiazolyl)-oxamate.

3. Compound of claim 1 which is ethyl-(4-phenyl-2-thiazolyl)-oxamate,

4. Compound of claim 1 which is ethyl-(4-p-chlorophenyl-2-thiazolyl)-oxamate.

5. Compound of claim 1 which is ethyl-(4-p-methoxyphenyl-2-thiazolyl)-oxamate.

6. Compound of claim 1 which is benzyl-(4-m-methylphenyl-2-thiazolyl)-oxamate.

7. Compound of claim 1 which is benzyl-(4-o-bromophenyl-2-thiazolyl)-oxamate.

8. Pharmaceutical composition useful for its allergic inhibitive characteristics, comprising an effective amount of a compound of claim 1 or claim 2 in combination with a pharmaceutically-acceptable carrier.

9. Pharmaceutical composition useful in the treatment of asthma, comprising an effective amount of a compound of claim 1 or claim 2 in combination with a pharmaceutically-acceptable carrier.

10. Method for the treatment of allergic manifestations, comprising administering to a patient subject thereto an effective amount of a compound according to claim 1 or claim 2 or a composition according to claim 8.

11. Method for the treatment of asthma, comprising administering to a patient subject thereto an effective amount of a compound according to claim 1 or claim 2 or a composition according to claim 9.

* * * * *

UNITED STATES PATENT AND TRADEMARK OFFICE
CERTIFICATE OF CORRECTION

PATENT NO. : 4,246,271

DATED : January 20, 1981

INVENTOR(S) : Henri Cousse, Gilbert Mouzin, Jean-Pierre Tarayre and Silvano Casadio It is certified that error appears in the above-identified patent and that said Letters Patent are hereby corrected as shown below:

[56] References Cited, U.S. PATENT DOCUMENTS, line 1; "6/1966" should read -- 6/1976 -- Original Document, patent No. 3,966,965.

Col. 3, line 9; "water, 15%" should read -- water. 15% --

Col. 5, lines 59 & 60; "(d) (intravenous simultaneously with d)." should read -- (d) intravenous simultaneously with (d). --

Col. 8, lines 25 & 26; "(4-p-methox-yphenyl-2-thiazolyl)" should read -- (4-p-methoxy-phenyl-2-thiazolyl) -- (incorrectly hyphenated)

Signed and Sealed this

Second Day of June 1981

[SEAL]

Attest:

RENE D. TEGTMEYER

Attesting Officer

Acting Commissioner of Patents and Trademarks